United States Patent [19]

Furnish

[11] Patent Number: 5,788,630

[45] Date of Patent: Aug. 4, 1998

[54] RIB RETRACTOR

[75] Inventor: Gregory R. Furnish, Lawrenceville, Ga.

[73] Assignee: Genzyme Corporation, Framingham, Mass.

[21] Appl. No.: 794,232

[22] Filed: Jan. 30, 1997

Related U.S. Application Data

[63] Continuation-in-part of Ser. No. 719,612, Sep. 25, 1996.

[51] Int. Cl.$^6$ .................................................. A61B 17/02
[52] U.S. Cl. ............................................................ 600/232
[58] Field of Search ................................. 600/201, 210, 600/215, 216, 219, 222, 227, 231, 232, 235, 233

[56] References Cited

U.S. PATENT DOCUMENTS

| | | |
|---|---|---|
| 4,156,424 | 5/1979 | Burgin . |
| 4,239,036 | 12/1980 | Krieger ........................... 600/216 X |
| 4,627,421 | 12/1986 | Symbas et al. . |
| 4,726,356 | 2/1988 | Santilli et al. . |
| 4,747,394 | 5/1988 | Watanabe . |
| 4,829,985 | 5/1989 | Couetil . |
| 4,852,552 | 8/1989 | Chaux . |
| 4,989,587 | 2/1991 | Farley . |
| 5,052,373 | 10/1991 | Michelson ........................ 600/232 X |
| 5,067,477 | 11/1991 | Santangelo ....................... 600/227 X |
| 5,167,223 | 12/1992 | Koros et al. . |
| 5,365,921 | 11/1994 | Bookwalter et al. ............... 600/232 |
| 5,616,117 | 4/1997 | Dinkler et al. .................... 600/232 |

FOREIGN PATENT DOCUMENTS

| | | |
|---|---|---|
| 792620 | 9/1997 | European Pat. Off. . |
| 473451 | 1/1915 | France ........................... 600/232 |

OTHER PUBLICATIONS

Promotional Literature (catalog) Aesculap Instruments Corp., (Feb., 1983).

Promotional Literature, T. Koros Surgical Instruments Corp., (1994).

Promotional Literature, Miltex (date unknown).

Promotional Literature, Pilling Surgical Instruments, A Rusch Inter. Co., (1993).

*Primary Examiner*—Jeffrey A. Smith
*Attorney, Agent, or Firm*—Needle & Rosenberg, P.C.

[57] ABSTRACT

An improved rib retractor adapted to contact adjacent ribs in a person through a thoracotomy incision comprising a longitudinally-extending rack with two support members, each having a longitudinal edge. The longitudinal edge of each of the support members is attached to the rack wherein at least one of the support members is movable along a portion of the length of the rack so that the support members are longitudinally movable relative to each other. A pair of blunt blades is provided, each adapted to contact a selected one of the ribs in the patient. A hinge rotatingly connects a portion of each of the support members to a portion of each of the blades. The blades are rotatable at least partially about an axis, such that each of the blades rotates between a first position, in which at least a section of the blade is oriented substantially parallel to the length of the rack and may be disposed above the incision of the person, and a second position, in which at least a section of the blade is disposed into the incision and the contact side of the body portion is oriented to engage a selected rib. The hinges allow the blades, when in the closed position, to contact each other, so that both of the blades simultaneously rotate from the first position to the second position as the blades are moved toward each other after engagement with each other. The present invention also includes a pawl that selectively engages the rack so the blades can freely move along the rack or be held at a desired separation distance.

18 Claims, 5 Drawing Sheets

RIB RETRACTOR

This application is a continuation-in-part application of application Ser. No. 08/719,612, filed Sep. 25, 1996, which is pending.

BACKGROUND OF THE INVENTION

1. Field of the Invention

The present invention relates to the field of thoracic surgery. In particular, the invention relates to an improved rib retractor for use in thoracic surgery, e.g., coronary artery bypass or mitral valve replacement surgery and the like.

2. Background Art

Various retractors for maintaining access to thoracotomy incisions such as, e.g., the Finochietto rib retractors are known in the art. Likewise, retractors for use in sternotomy incisions are also known in the art. U.S. Pat. No. 4,852,552, for example, discloses a sternal retractor for use in internal mammary artery surgery. Generally, such rib retractors or sternotomy retractors are comprised of two substantially perpendicular retractor blades which remain generally perpendicular in their operative or deployed position. This substantially perpendicular orientation of the blades limits the surgeons mobility and access to the surgical field. This is especially true for procedures that are performed deep within the thoracic cavity.

Often, the retractor blades are fenestrated or open over at least a portion of their surface area and are not contoured for an "anatomical fit" against the rib. Such a design concentrates pressure and often results in increased trauma to the intercostal veins, arteries, nerves and musculature. Fenestrated or open blades likewise increase trauma because the intercostal tissue, under pressure, tends to be extruded through the openings, thereby incurring damage via the sharp edges of the blade openings or via blunt trauma resulting from contact with instruments during the procedure. This fenestrated blade design also reduces the surgical field due to tissue impingement and can increase hemorrhage at the incision site making it more difficult for the surgeon to visualize deeper structures.

In order to increase the surgeons access to the surgical field, standard Finochietto retractors have been limited to a single ratcheting mechanism which is attached to the retractor blade via a substantially perpendicular retractor arm. This design attempts to create a window or space between the rachet and retractor blade where the surgeon can access the surgical site. However, such an arrangement often results in unequal distribution of force and, actually, can increase the total amount of force necessary to maintain adequate adduction of the ribs for access to the surgical site.

Prior to the present invention, there has not been a retractor designed especially for the narrow window presented via an intercostal thoracotomy approach which overcomes the above disadvantages of the prior art. Prior to the present invention there existed a need in the art for a rib retractor which would provide increased surgical access field with an increased range of motion for the long shafted surgical instruments that are often utilized deep within the thoracotomy, especially with cardiac procedures. There also exists a need for a retractor which uniformly distributes force over the retractor blade area and which minimizes trauma to the intercostal tissue.

OBJECTS OF THE INVENTION

Accordingly, it is an object of the invention to provide a rib retractor which provides an increased surgical access field without an associated increase in pressure or trauma to the intercostal tissue.

It is also an object of the invention to provide a rib retractor wherein the retractor blades are anatomically contoured to fit the ribs and is self-adjusting when deployed to distribute force over the surface area of the blades evenly.

Another object of the invention is to provide retractor blades having a smooth convex surface which protects surgical instruments from damage, and is contoured to the anatomical shape of the ribs.

It is further a object of the invention to provide a rib retractor wherein the ratcheting or adducting force is evenly distributed over the length of the retractor mounting arm.

Another object of the invention is to provide a rib retractor which can selectively lock the retractor blades in a predetermined orientation prior to and after deployment and wherein there exists a means for providing uniform rotation of blades from an insertion or closed position to the operative or open position.

Still another object of the invention is to provide a means for selectively engaging the rack along which the blades longitudinally move relative to each other. Thus, the blades can freely move along the rack or be held in at a desired separation distance.

These and other objects of the invention will be apparent to the skilled artisan.

SUMMARY OF THE INVENTION

The present invention provides an improved rib retractor, having a longitudinal axis that is adapted to contact adjacent ribs in a person through a thoracotomy incision. The apparatus of the invention is comprised of a longitudinally-extending rack having a preselected length with two support members each having a longitudinal edge. Also provided is a means for attaching the longitudinal edge of each of the support members to the rack, wherein at least one of the support members is movable along a portion of the length of the rack so that the support members are longitudinally movable relative to each other. A pair of blunt blades is provided, with each blade comprising a body portion having a top edge, a contact side, and an opposed external side. The contact side of each blade is adapted to contact a selected one of the ribs in the subject person.

A hinge rotatingly connects a portion of each of the support members to a portion of the body portion of an associated one of the blades adjacent the top edge of the body portion. The hinge has an axis of rotation disposed substantially perpendicular to the longitudinal axis of the rib retractor. The body portion is rotatable at least partially about an axis, such that each of the body portions rotates between a first position, in which at least a section of the body portion is oriented substantially parallel to the length of the rack and may be disposed above the incision of the person, and a second position, in which at least a section of the body portion may be disposed into the incision and the contact side of the body portion is oriented to engage a selected rib.

Also provided are means for detachably engaging the blades with each other when the blades are in a closed position. In the closed position, a portion of the external side of the body portions contact each other, so that both of the blades simultaneously rotate from the first position to the second position as the blades are moved toward each other after engagement with each other.

The present invention also provides a means for securing the blades at selected points along the length of the rack as the blades longitudinally move relative to each other and a means for selectively disengaging the securing means. When the securing means has been disengaged, the movable blade can freely slide along the rack and, when engaged, the blades are held in at a desired longitudinal separation distance relative to each other.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used.

The present invention comprises a rib retractor 10 for use in thoracic surgery, specifically heart surgery. The rib retractor 10 is adapted to contact two adjacent ribs B in a person through an incision and separate the adjacent ribs B apart from each other. Once the ribs B are separated, then a surgeon can perform a desired surgical procedure, such as coronary artery bypass surgery, mitral valve replacement or the like. As one of skill in the art will appreciate, the rib retractor of the present invention can also be utilized as a sternal retractor for maintaining thoracic cavity access via a sternotomy incision or utilized in the abdominal midline, e.g., for maintaining access to the abdomen via a celiotomy incision or the like.

Figure 2:
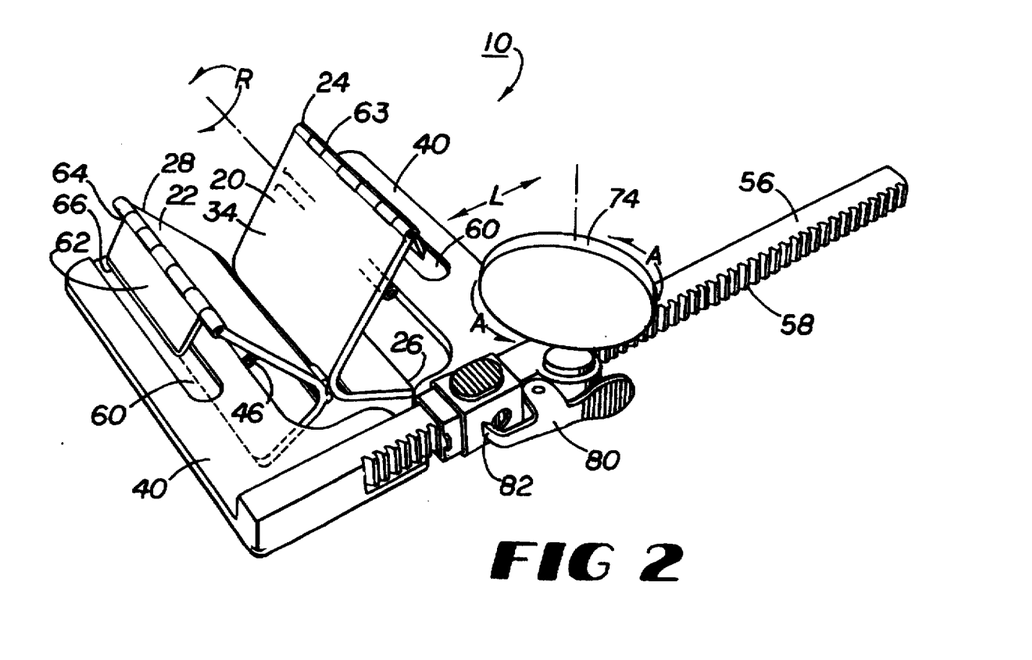
FIG. 2 is a perspective view of an alternate embodiment FIG. 1 without latches showing the blades having rotated to the second position.

The rib retractor 10, which has a longitudinal axis L, comprises a pair of blunt blades 20, a means for moving the blades 20 relative to each other substantially along the longitudinal axis L of the rib retractor 10, and a means for connecting the each of the blades 20 to the moving means so that the blades 20 are rotatable at least partially about an axis R. Axis R, shown for example in FIG. 2, is oriented substantially perpendicular to the longitudinal axis L of the rib retractor 10 and substantially parallel to the ribs B of the patient.

Figure 1:
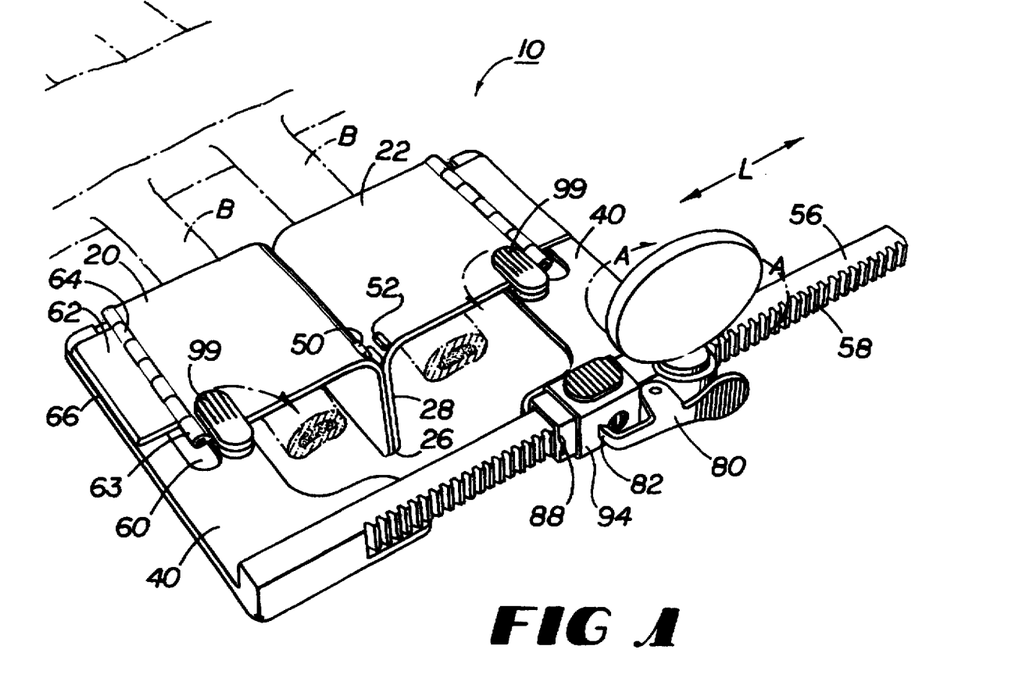
FIG. 1 is perspective view of the present invention showing the blades of the rib retractor in the first position.

Each of the blades 20 comprises a body portion 22 having a top edge 24, an opposite bottom edge 26, and two opposed side edges 28. The body portion 22 of each blade 20 also has a contact side 30 and an opposed external side 32. Preferably, at least a section of the body portion 22 is curved in cross section along a plane parallel to the longitudinal axis L of the rib retractor 10. As best shown in FIG. 1, the body portion 22 of the preferred blade 20 is "L" shaped in cross section so that each of the body portions 22 has a first section 34, a second section 36, and a curved portion 38 therebetween. The second section 36 is oriented substantially perpendicular to the first section 34. When the blades 20 are rotated downwardly about their axis of rotation R approximately forty-five degrees (45°), as shown comparing FIG. 2 to FIG. 1, the two body portions 22 form an hour glass profile in cross section. However, other cross-sectional shapes of the blades 20 are contemplated, such as those having a semi-circle or substantially linear cross section.

The moving means allows the blades 20 to move between a closed position and an open position. In the closed position, shown in FIGS. 1 and 2, a portion of the external side 32 of each of the body portions 22 contact each other. In the open position, shown in FIGS. 3, 4, and 5, the body portions 22 are spaced apart from each other.

Figure 3:
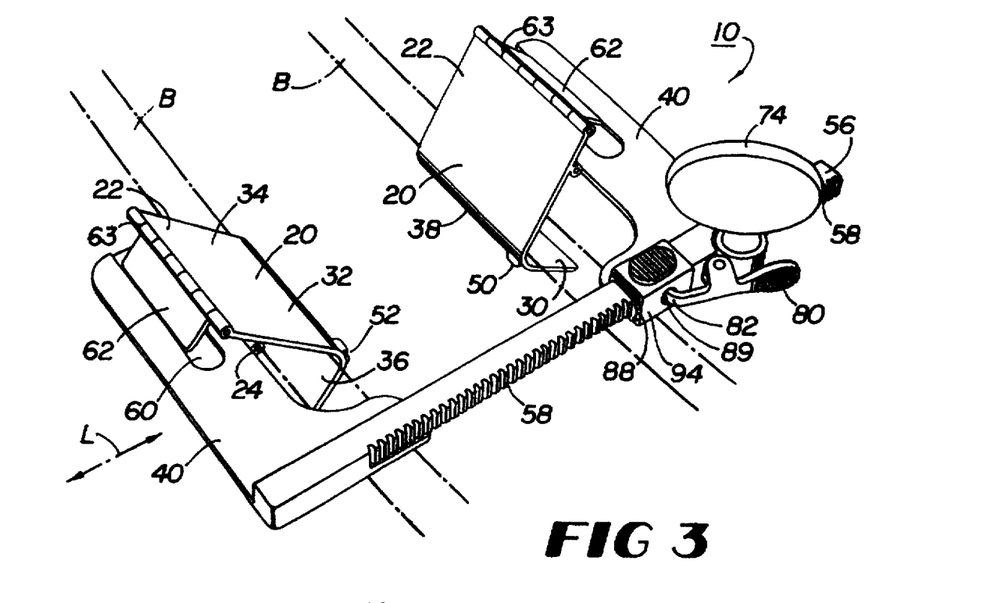
FIG. 3 is a perspective view of FIG. 2 showing the blades having moved to the open position while in the second position and engaging the ribs of the patient.
Figure 4:
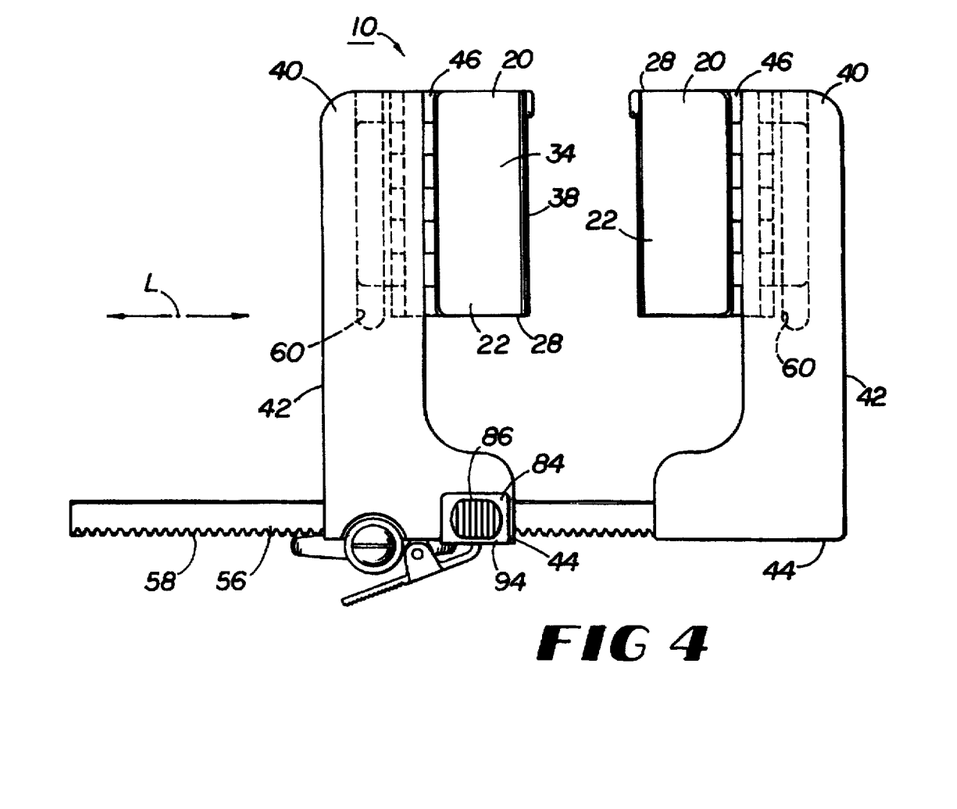
FIG. 4 is a bottom plan view of the rib retractor shown in FIG. 3.
Figure 5:
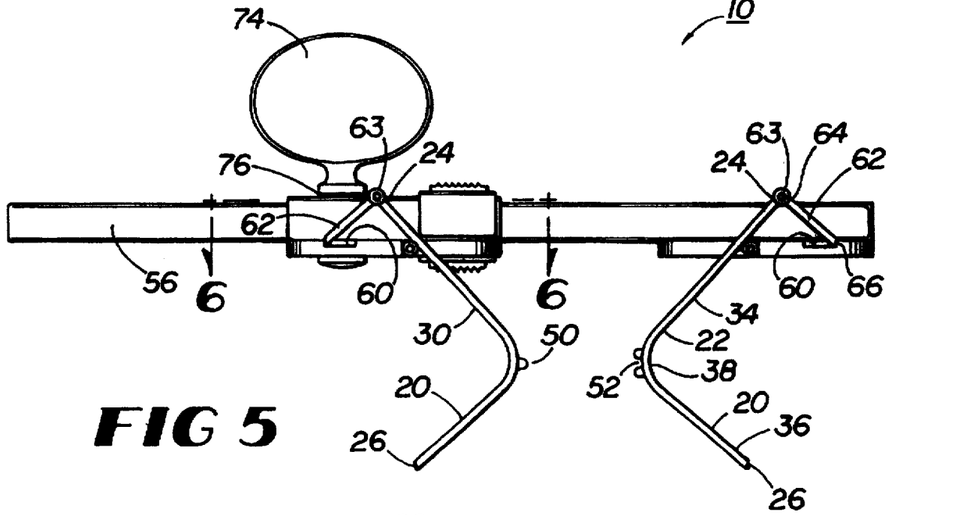
FIG. 5 is a side view of the rib retractor shown in FIG. 2.

The connecting means allows each body portion 22 to rotate at least partially about its axis of rotation R. Each of the body portions 22 is rotatable between a first position and a second position, which are shown in FIGS. 1 and 2, respectively. In the first position, at least a section of the body portion 22—here the first section 34 of the blade 20—is disposed above or at the same height as its axis of rotation R. When in the second position, a portion of that section which was previously disposed above or at the same height as the axis of rotation R is now disposed below that axis of rotation R, as shown in FIGS. 2, 3, and 5. Stated differently, at least a section of the body portion 22 in the first position is disposed above the incision and at least a section of the body portion 22 in the second portion is disposed into the incision. In the second position, the contact side 30 of each body portion 22 preferably is oriented to engage one rib B.

It is preferred that each of the connecting means comprises a support member 40, which has a lateral edge 42 and a longitudinal edge 44, and a hinge 46 that rotatingly connects a portion of the support member 40 to a portion of one body portion 22 adjacent its top edge 24. Thus, there are two hinges 46 in which each hinge 46 is attached to a different body portion 22 and support member 40. Each hinge 46 rotates the associated body portion 22 about its respective axis of rotation R.

The rib retractor 10 of the present invention preferably comprises a means for detachably engaging the blades 20 with each other when the blades 20 are in the closed position. Once engaged, both blades 20 are simultaneously rotatable from the first position to the second position as the support members 40 are moved closer toward each other, which is best shown comparing FIGS. 1 and 2.

The preferred detachably engaging means comprises a protrusion 50 disposed on the external side 32 of one of the body portions 22 and an indentation 52 disposed in the external side 32 of the other body portion 22. The indentation 52 is of a size to complementarily receive the protrusion 50 therein. When the blades 20 move from the open position to the closed position, the protrusion 50 engages and interlocks with the indentation 52, which is shown in FIG. 1. After the protrusion 50 engages the indentation 52, the moving means continues to move the support members 40 toward each other. Since the blades 20 are engaged with each other, the additional movement causes the blades 20 to rotate, or pivot, about their respective axis of rotation R from the first position to the second position, which is shown in FIG. 2. Once in the second position, the blades 20 are in the preferred position for use as a rib retractor 10 because they are disposed to have an hour glass configuration in cross section. Referring now to FIG. 3, the blades 20 are disposed to cup the ribs B so that the ribs B contact a portion of the curved portion 38 of the blades 20.

Once in the second position, the rib retractor 10 preferably further comprises a means for locking each of the body portions 22 in that orientation. Referring back to FIG. 2, each of the support members 40 has a detent 60 therein and each of the connecting means further comprises a locking member 62 connected to each blade 20. The locking member 62 has a first end 64 pivotally depending from the top edge 24 of one of the body portions 22, such as by a hinge 63, and an opposite second end 66 that complementarily engages the detent 60 in the associated support member 40. With the locking member 62 engaged with the detent 60, the body portion 22 is locked in the second position. That is, the locking member 62 securely engages the detent 60 when a force is applied to the contact side 30 of the body portion 22 below the hinge 46, such as when the contact side 30 of the blade 20 contacts the rib B. Thus, when the moving means moves the blades 20 to the open position, the blades 20 remain locked in the second position. As those skilled in the art will appreciate, when the second end 66 is disengaged from the detent 60, the body portion 22 is rotatable about axis R.

To guide longitudinal movement of the blades 20, the moving means preferably comprises a longitudinally-extending rack 56 having a length and a means for attaching a longitudinal edge 44 of each of the support members 40 to the rack 56. At least one of the support members 40 should be movable along a portion of the length of the rack 56 so that the support members 40 are longitudinally movable relative to each other. As shown in FIGS. 1–5, only one of the support members 40 is movable and the other support member 40 is fixedly attached to the rack 56, such as by a weld. However, it is contemplated that both of the blades 20 can be movable along a portion of the length of the rack 56.

The rack 56 preferably has a plurality of teeth 58 longitudinally disposed along at least a portion of its length. Now referring to FIGS. 5, 6, and 7, the attaching means of the support member 40 that is movable along the rack 56 comprises a pinion 70 having a plurality of teeth 72 therein, a means for positioning the pinion 70 relative to the support member 40, and a handle member 74 to rotate the pinion 70. The teeth 72 of the pinion 70 matingly engage the teeth 58 of the rack 56 and the positioning means positions the pinion 70 so that its teeth 72 rotatably and movably engage the teeth 58 of the rack 56. The handle member 74 has a bottom end 76 fixedly attached to a portion of the pinion 70 so that rotation of the handle member 74 causes the pinion 70 to rotate. This rotation of the pinion 70 correspondingly causes the support member 40 to move longitudinally along at least a portion of the length of the rack 56 as the teeth 72 of the pinion 70 engage the teeth 58 of the rack 56. Rotation of the handle member 74 is represented by arrows A in FIGS. 1 and 2. FIG. 1 shows the handle member 74 being rotated to move the support members 40 toward each other and FIG. 2 shows rotation so that support members 40 move away from each other.

Figure 6:
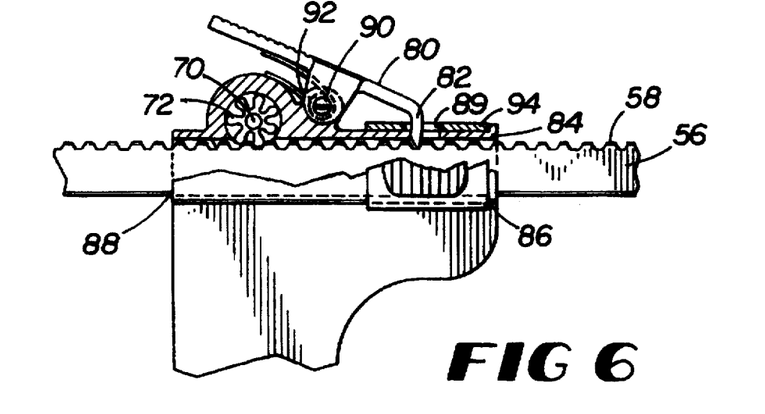
FIG. 6 is a top plan view of the securing means and the first embodiment of the selective disengaging means of the present invention taken along line 6—6 in FIG. 5, in which the selective disengaging means is in the engaged position.
Figure 7:
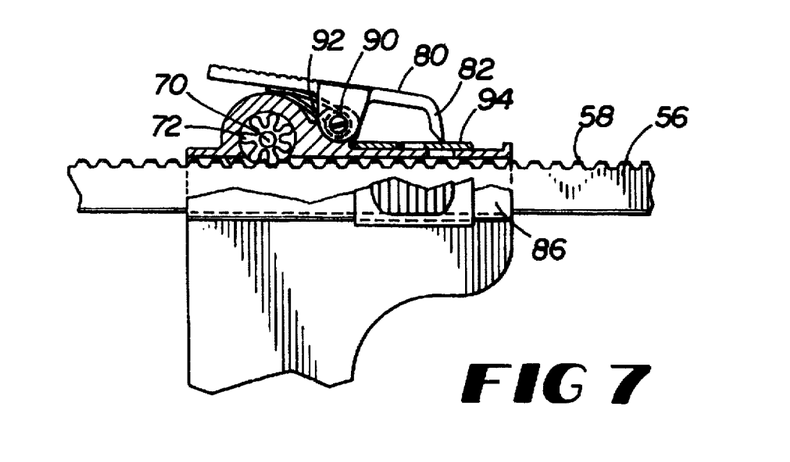
FIG. 7 is an alternate view of FIG. 6, in which the selective disengaging means is in the disengaged position.
Figure 8:
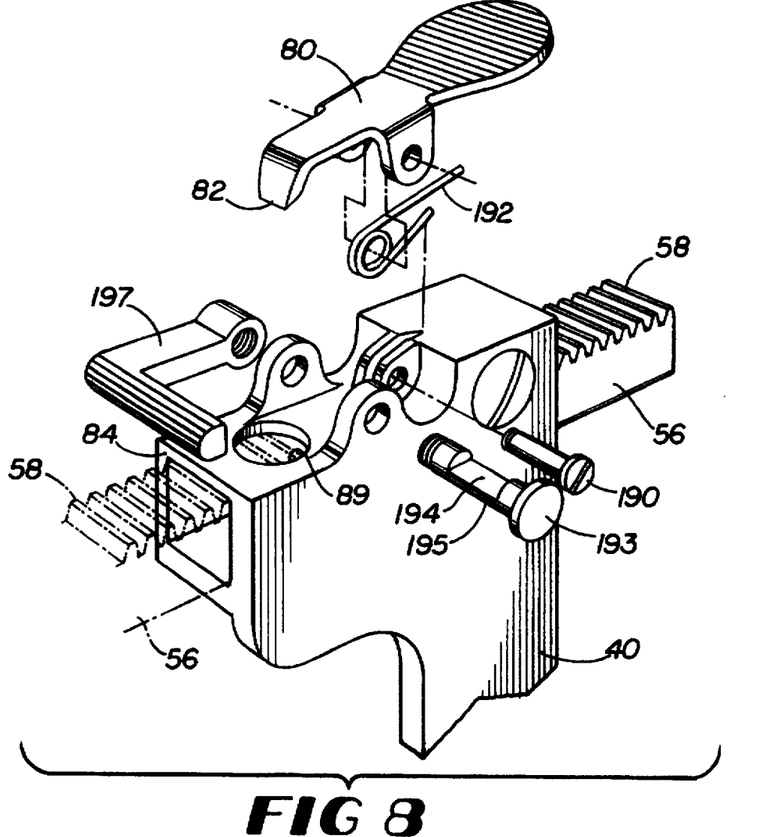
FIG. 8 is a fragmentary exploded perspective view of the second embodiment of the selective disengaging means of the present invention.
Figure 9:
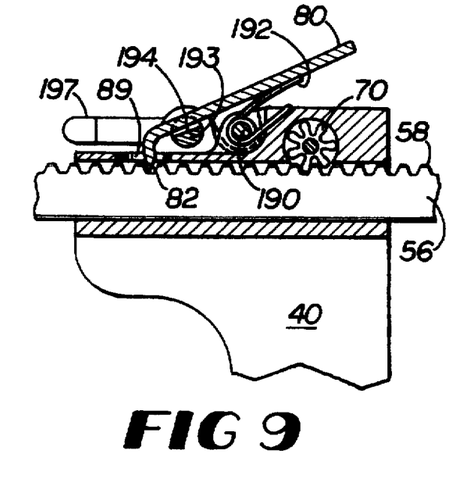
FIG. 9 is a top plan view of the securing means and the selective disengaging means shown in FIG. 8, in which the selective disengaging means is in the engaged position.
Figure 10:
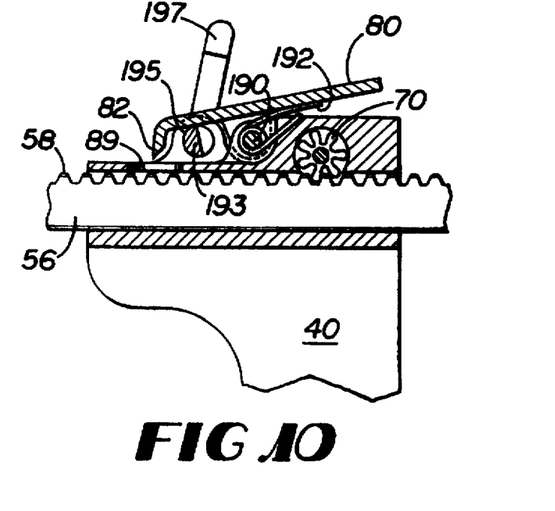
FIG. 10 is an alternate view of FIG. 9, in which the selective disengaging means is in the disengaged position.

Preferably, the present invention also comprises a means for securing the support member 40 at selected points throughout a range of locations along the length of the rack 56 and a means for selectively disengaging the securing means. FIGS. 6 and 7 show a first embodiment and FIGS. 8–10 show a second embodiment of the selective disengaging means, respectively.

Referring first to FIGS. 6 and 7, an aligning member 84 of the attaching means and a pawl arm 80 having a pawl tooth 82 of the securing means are shown. The aligning member 84 has an exterior surface 86 and defines a bore 88 therethrough. The bore 88 is of a size to slidably receive the rack 56 therein. The pawl tooth 82 is of a size to be complementarily received intermediate two adjacent teeth 58 of the rack 56. A portion of the exterior surface 86 of the attaching member preferably is fixedly attached to the longitudinal edge of the support member 40 and another portion of the exterior surface 86 has a slot 89 therethrough communicating with the bore 88. The slot 89 is disposed over the teeth 58 in the rack 56 to allow communication therethrough.

The securing means also preferably comprises a means for pivotally mounting the pawl arm 80 to a portion of the exterior surface 86 of the aligning member 84 so that the pawl tooth 82 is movable to communicate selectively with the teeth 58 of the rack 56 through the slot 89 of the aligning member 84. Alternatively, it is contemplated that the pawl tooth 82 can communicate with the teeth 58 in the rack 56 independent of using the slot 89, such as the pawl tooth 82 extending off one end of the attaching member to communicate with the teeth 58. Still referring to FIGS. 6 and 7, the pivotal mounting means is a pin 90 attached to the attachment member about which the pawl arm 80 rotates, although other pivotal mounting means can be used, such as a hinge (not shown), swivel (not shown) and the like.

It is also preferred that the securing means further comprises a means for biasing the pawl tooth 82 of the pawl arm 80 toward the teeth 58 of the rack 56 so that the pawl tooth 82 is capable of selectively engaging the teeth 58 of the rack 56. The biasing means is a spring clip 92, or torsional spring, having one end fixedly attached to a portion of the exterior surface 86 of the aligning member 84 and another end fixedly attached to a portion of the pawl arm 80. The spring clip 92 biases the pawl tooth 82 into the teeth 58 of the rack 56, as shown in FIG. 6. As will be appreciated, the downward pressure of the surgeon's finger on the pawl arm 80 toward the pinion 70 is sufficient to overcome the opposing force of the spring clip 92, which causes the pawl tooth 82 to move upwardly and away from the teeth 58 in the rack 56. FIG. 7 shows the spring clip 92 biasing the pawl tooth 82 downwardly, although the pawl tooth 82 is not engaging the teeth 58 of the rack 56. Other biasing means include a coiled spring (not shown), torque tube (not shown), and the like.

The first embodiment of the selective disengaging means, shown in FIGS. 6 and 7, comprises a pawl detachment member 94 slidably mounted over at least a portion of the exterior surface 86 of the aligning member 84. The pawl detachment member 94 is movable between a disengaged position and an engaged position. FIG. 7 shows the disengaged position, in which the pawl detachment member 94 is disposed over at least a portion of the slot 89 in the aligning member 84 intermediate the pawl tooth 82 and the teeth 58 of the rack 56 to prevent communication therewith. Referring back to FIG. 6, the pawl detachment member 94, which is in the engaged position, is disposed so that the pawl tooth 82 can communicate with the teeth 58 of the rack 56 through the slot 89 of the aligning member 84.

The second embodiment of the selective disengaging means, shown in FIGS. 8-10, comprises a barrel member 193, which is rotatably mounted to the aligning member 84 intermediate the pawl arm 80 and the rack 56, and a means for rotating the barrel member 193. The barrel member 193 has both a latch surface 194 and a delatch surface 195 which are best shown in FIG. 8. The rotating means preferably comprises a lever 197 fixedly attached to a portion of the barrel member 193. This selective disengaging means is preferred compared to the first embodiment because it is easier for the surgeon to move the lever 197 than to slide the pawl detachment member.

Rotation of the lever 197 shifts the barrel member 193 between the disengaged position and the engaged position. FIG. 9 shows the engaged position, in which the barrel member 193 is rotated so that the latch surface 194 of the barrel contacts the pawl arm 80. Since the latch surface 194 is truncated or lower relative to the delatch surface 195, the pawl tooth 82, urged by the biasing means, communicates with the teeth 58 of the rack 56 through the slot 89 of the aligning member 84. In the disengaged position shown in FIG. 10, the delatch surface 195 of the barrel member 193 contacts and raises the pawl arm 80 against the opposing force of the biasing means so that the pawl tooth 82 is prevented from communicating with the teeth 58 of the rack 56. Thus, in the disengaged position, the aligning member 84 and its attached support member 40 are freely movable along a portion of the length of the rack 56 since the pawl tooth 82 does not contact the teeth 58 of the rack 56. Conversely, when in the engaged position, the pawl tooth interfacing with teeth 58 in the rack 56 prevent this free movement.

Specifically, referring back to FIGS. 6 and 7, it is preferred that the pawl arm 80 is longitudinally oriented and the pawl tooth 82 is disposed intermediate the opposed support member 40 and the pivotal mounting means. Thus, when the pawl tooth 82 engages the teeth 58 of the rack 56 in the engaged position, the support member 40, based on the position of the pivotal mounting means and the biasing means, is movable longitudinally away from the other support member 40 and is prevented from moving toward the other support member 40 while the pawl tooth 82 is engaged with the teeth 58 of the rack 56.

Figure 11:
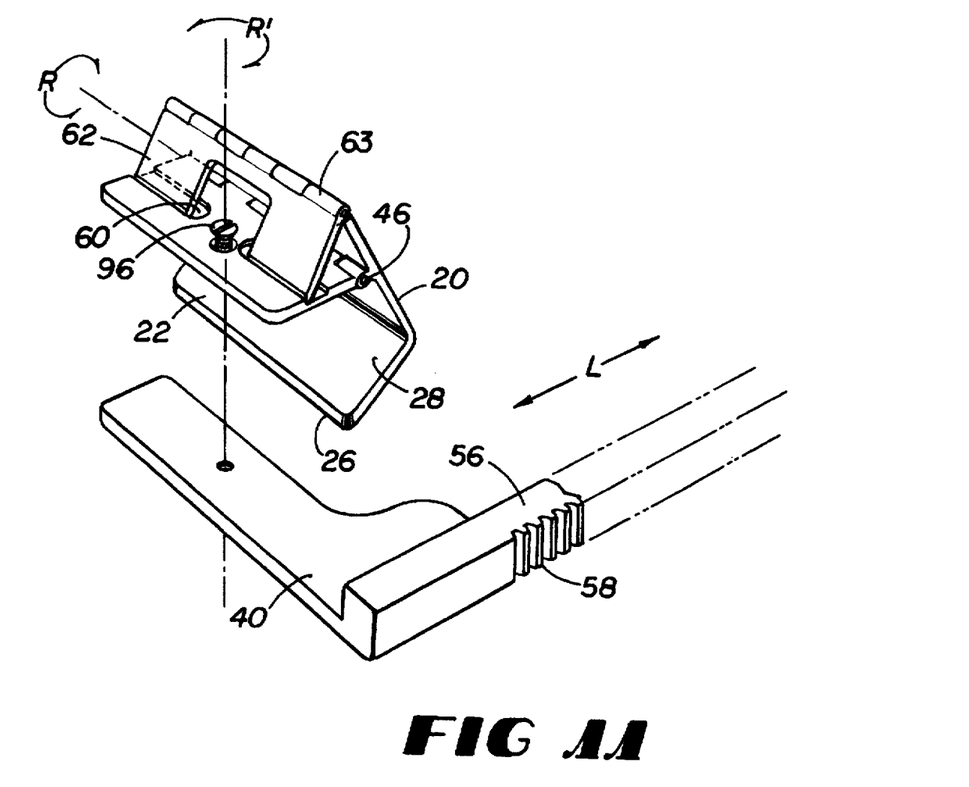
FIG. 11 is an alternate perspective view of FIG. 1 showing a swivel connecting the blade to the support member.

As shown in FIG. 11, it is also preferred that at least one of the connecting means further comprises a means for rotatably mounting the hinge 46 to the support member 40 so that the hinge 46 and body portion 22 attached thereto are pivotally connected to a portion of the support member 40. The rotatably mounting means has an axis of rotation R' substantially perpendicular to the axis R about which the hinge 46 rotates and also substantially perpendicular to the longitudinal axis L of the rib retractor 10. Preferably, the rotatably mounting means comprises a hinge plate 97 into which the detent 60 and hinge are formed and a swivel 96 having a top end engaging a portion of the hinge plate 97 and an opposite bottom end engaging the support member 40 so that the hinge plate 97 is rotatable relative to the support member 40. The rotatably mounting means can entail other means, such as a pin (not shown), another hinge (not shown), or other device to rotatably couple the hinge plate 97 to the support member 40 so that the blade 20 may pivot about axis R'. The rotatably mounting means allows the blades 20 to conform to the shape of the non-parallel ribs B, which reduces the stresses on the blades 20 and the ribs B of the patient.

Figure 12:
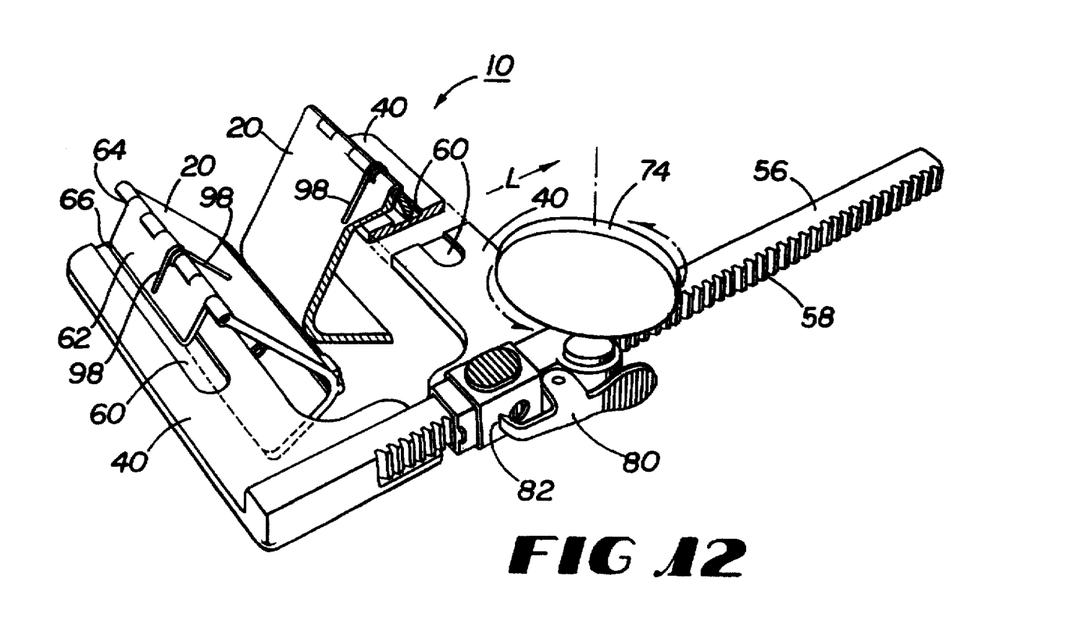
FIG. 12 is an alternate view of FIG. 1 showing a spring member used with the blades.

Referring now to FIG. 12, an alternate embodiment of the rib retractor 10 includes a spring 98 that biases the blade 20 and the locking member 62 so that the locking member 62 and the first section 34 of the blade 20 form a desired angle therebetween. The angle positions the locking member 62 to engage the detent 60 when the blade 20 is at the second position. This biasing of the locking member 62 relative to the blade 20 allows the surgeon to engage the first end 64 of the locking member 62 with the detent 60 quickly.

Referring back to FIG. 1, the rib retractor 10 of the present invention can further comprise a latch 99 that is pivotally mounted to each support member 40 adjacent the first section 34 of the blade 20. As will be appreciated, the latch 99 can swing between a securing position, in which the latch 99 holds the blade 20 in the first position, and a release position, in which the latch 99 allows the blade 20 to rotate about its axis of rotation R. The latches 99 are in the securing position before the blades 20 are rotated from the first position to the second position and then the latches 99 remain in the release position.

As discussed above, the body portion 22 of the blades 20 are preferably "L" shaped in cross section. When the blades 20 are in the first position, the first section 34 is substantially parallel to the longitudinal axis L of the rib retractor 10 and the second section 36 depends downwardly therefrom and, when in the second position, the first and second sections 34, 36 are rotated downwardly approximately forty-five degrees from the first position. This blade 20 design provides many advantages for use in thoracic surgery. The hour glass profile allows greater access through the incision and into the body, specifically the intercostal area of the patient, than other prior art designs. The design of the blades 20 also requires less spreading of the ribs B to access the intercostal area to operate than other designs. Accordingly, with less separation required, there is less invasion into the body and less trauma to the intercostal spaces. The blades 20 thus result in less damage to arteries, veins, and nerves during a surgical procedure.

The advantageous blade design works in conjunction with the rib retractor 10 rotating from the first position to the second position. The surgeon makes a small incision initially instead of a larger one required for prior art devices. The surgeon then places the rib retractor 10 on the person, as shown in FIG. 1. The surgeon turns the handle member 74 so that the support members 40 move toward each other, thereby causing the blades 20 to rotate from the first position to the second position, as shown in FIG. 2. Accordingly, the second section 36 of the blades 20 move inwardly into the incision and can be locked in the second position. As will be appreciated, the incision would have to be wider to initially insert the blades 20 directly into it when in the second position. And, once the blades 20 rotate to the second position, they provide the greatest access with the least trauma.

Although the present invention has been described with reference to specific details of certain embodiments thereof, it is not intended that such details should be regarded as limitations upon the scope of the invention except as and to the extent that they are included in the accompanying claims.

What is claimed is:

1. An apparatus, having a longitudinal axis, comprising:
   a. a pair of blunt blades, each of said blades comprising a body portion having a top edge, a contact side, and an opposed external side;
   b. a rack for longitudinally moving said blades relative to each other between a closed position, in which a portion of the external side of each of said body portions contact each other, and an open position, in which said body portions are spaced apart from each other, said rack having a length and teeth therein;
   c. a pair of support members, each of said support members having a longitudinal edge adapted for connecting the body portion of each of said blades to a portion of said rack;
   d. means for attaching the respective longitudinal edge of each of said support members to said rack, wherein at least one of said support members is movable along a portion of the length of said rack;
   e. means for securing each of said support members that is movable along said rack at selected positions along the length thereof; and
   f. means for selectively disengaging said securing means,
   wherein said attaching means for each of said support members that is movable comprises an aligning member having an exterior surface and defining a bore therethrough, said bore being of a size to slidably receive said rack therein, a portion of said exterior surface being fixedly attached to the longitudinal edge of said support member and another portion of said exterior surface having a slot therethrough communicating with said bore, said slot being disposed over the teeth in said rack, and
   wherein said securing means comprises:
      i. a pawl arm having a pawl tooth, said pawl tooth complementarily to a space intermediate two adjacent teeth of said rack;
      ii. means for pivotally mounting said pawl arm to a portion of the exterior surface of said aligning member so that said pawl tooth is movable to communicate with the teeth of said rack through the slot of said aligning member; and
      iii. means for biasing the pawl tooth of said pawl arm toward the teeth of said rack so that said pawl tooth is capable of selectively engaging the teeth of said rack,
   wherein said selective disengaging means comprises:
      i. a barrel member rotatably mounted to said aligning member intermediate said pawl arm and said rack, said barrel member having a latch surface and a delatch surface, said barrel being rotatable between a disengaged position, in which the delatch surface of said barrel contacts a portion of said pawl arm so that said pawl tooth is prevented from communicating with the teeth of said rack, and an engaged position, in which the latch surface of said barrel contacts said pawl arm allowing said pawl tooth to communicate with the teeth of said rack through the slot of said aligning member; and
      ii. means for rotating said barrel member.

2. The apparatus of claim 1, wherein said rack has a plurality of teeth longitudinally disposed therein along at least a portion of its length, and
   wherein said attaching means of each of said support members that is movable comprises:
      a. a pinion having a plurality of teeth therein that matingly engage the teeth of said rack;
      b. means for positioning said pinion relative to said support member, wherein the teeth of said pinion rotatably and movably engage the teeth of said rack; and
      c. a handle member having a bottom end fixedly attached to a portion of said pinion so that rotation of said handle member causes said pinion to rotate which correspondingly causes said support member to move longitudinally along at least a portion of the length of said rack.

3. The apparatus of claim 1, wherein said rotating means comprises a lever fixedly attached to a portion of said barrel member, wherein rotation of said lever rotates said barrel member.

4. An apparatus, having a longitudinal axis, comprising:
   a. a pair of blunt blades, each of said blades comprising a body portion having a top edge, a contact side, and an opposed external side;
   b. a rack for longitudinally moving said blades relative to each other between a closed position, in which a portion of the external side of each of said body portions contact each other, and an open position, in which said body portions are spaced apart from each other, said rack having a length and teeth therein;
   c. a pair of support members, each of said support members having a longitudinal edge adapted for connecting the body portion of each of said blades to a portion of said rack;
   d. means for attaching the respective longitudinal edge of each of said support members to said rack, wherein at least one of said support members is movable along a portion of the length of said rack, wherein said attaching means for each of said support members that is movable comprises an aligning member having an exterior surface and defining a bore therethrough, said bore being of a size to slidably receive said rack therein, a portion of said exterior surface being fixedly attached to the longitudinal edge of said support member and another portion of said exterior surface having a slot therethrough communicating with said bore, said slot being disposed over the teeth in said rack;
   e. means for securing each of said support members that is movable along said rack at selected positions along the length thereof, wherein said securing means comprises:
      i. a pawl arm having a pawl tooth, said pawl tooth complementarily to a space intermediate two adjacent teeth of said rack;
      ii. means for pivotally mounting said pawl arm to a portion of the exterior surface of said aligning member so that said pawl tooth is movable to communicate with the teeth of said rack through the slot of said aligning member; and
      iii. means for biasing the pawl tooth of said pawl arm toward the teeth of said rack so that said pawl tooth is capable of selectively engaging the teeth of said rack; and
   f. means for selectively disengaging said securing means, wherein said selective disengaging means comprises a pawl detachment member slidably mounted over at least a portion of the exterior surface of said aligning member, said pawl detachment member being movable between a disengaged position, in which said pawl detachment member is disposed over at least a portion of the slot in said aligning member so that said pawl detachment member is disposed intermediate said pawl tooth and the teeth of said rack to prevent communication therewith, and an engaged position, in which said pawl detachment member is disposed so that said pawl tooth communicates with the teeth of said rack through the slot of said aligning member.

5. An apparatus, having a longitudinal axis, comprising:
 a. a pair of blunt blades, each of said blades comprising a body portion having a top edge, a contact side, and an opposed external side;
 b. a rack for longitudinally moving said blades relative to each other between a closed position, in which a portion of the external side of each of said body portions contact each other, and an open position, in which said body portions are spaced apart from each other, said rack having a length;
 c. a pair of support members, each of said support members having a longitudinal edge adapted for connecting the body portion of each of said blades to a portion of said rack;
 d. means for attaching the respective longitudinal edge of each of said support members to said rack, wherein at least one of said support members is movable along a portion of the length of said rack;
 e. means for securing each of said support members that is movable along said rack at selected positions along the length thereof;
 f. means for selectively disengaging said securing means; and
 g. means for detachably engaging said blades with each other when said blades are in the closed position so that both of said blades simultaneously rotate from the first position to the second position as said blades are moved toward each other after engaging with each other.

6. An apparatus, having a longitudinal axis, comprising:
 a. a pair of blunt blades, each of said blades comprising a body portion having a top edge, a contact side, and an opposed external side;
 b. means for longitudinally moving said blades relative to each other between a closed position, in which a portion of the external side of each of said body portions contact each other, and an open position, in which said body portions are spaced apart from each other;
 c. means for connecting the body portion of each of said blades to said moving means so that said body portions are rotatable at least partially about an axis substantially perpendicular to the longitudinal axis of said apparatus, wherein each of said body portions rotates between a first position, in which at least a section of said body portion is disposed above or at the same height as the axis about which said body part rotates, and a second position, in which a portion of that section of said body portion disposed above or at the same height as the axis of rotation is disposed below the axis of rotation, wherein each of said connecting means comprises:
  i. a support member having a longitudinal edge; and
  ii. a hinge rotatingly connecting a portion of said support member to a portion of the associated said body portion adjacent the top edge thereof, said hinge having an axis disposed along the axis about which said body portion rotates, wherein said rack has a plurality of teeth longitudinally disposed therein along at least a portion of its length, and wherein said moving means comprises;
   i. a longitudinally-extending rack having a length; and
   ii. means for attaching the respective longitudinal edge of each of said support members to said rack, wherein at least one of said support members is movable along a portion of the length of said rack so that said support members are longitudinally movable relative to each other, wherein said attaching means for each of said support members that is movable comprises an aligning member having an exterior surface and defining a bore therethrough, said bore being of a size to slidably receive said rack therein, a portion of said exterior surface being fixedly attached to the longitudinal edge of said support member and another portion of said exterior surface having a slot therethrough communicating with said bore, said slot being disposed over the teeth in said rack;
 d. means for securing said blades at selected longitudinal positions relative to each other, wherein said securing means comprises:
  i. a pawl arm having a pawl tooth, said pawl tooth complementarily to the space intermediate two adjacent teeth of said rack;
  ii. means for pivotally mounting said pawl arm to a portion of the exterior surface of said aligning member so that said pawl tooth is movable to communicate with the teeth of said rack through the slot of said aligning member; and
  ii. means for biasing the pawl tooth of said pawl arm toward the teeth of said rack so that said pawl tooth is capable of selectively engaging the teeth of said rack; and
 e. means for selectively disengaging said securing means, wherein said selective disengaging means comprises:
  i. a barrel member rotatably mounted to said aligning member intermediate said pawl arm and said rack, said barrel member having a latch surface and a delatch surface, said barrel being rotatable between a disengaged position, in which the delatch surface of said barrel contacts a portion of said pawl arm so that said pawl tooth is prevented from communicating with the teeth of said rack, and an engaged position, in which said barrel member is rotated so that the latch surface of said barrel contacts said pawl arm allowing said pawl tooth to communicate with the teeth of said rack through the slot of said aligning member; and
  ii. means for rotating said barrel member.

7. The apparatus of claim 6, wherein said rotating means comprises a lever fixedly attached to a portion of said barrel member, wherein rotation of said lever rotates said barrel member.

8. The apparatus of claim 6, further comprising means for locking each of said body portions in the second position.

9. The apparatus of claim 6, wherein at least one of said connecting means further comprises means for rotatably mounting said hinge to said support member so that said hinge and body portion attached thereto are pivotally connected to a portion of said support member, said pivotal mounting means having an axis of rotation perpendicular to both the axis about which said hinge rotates and perpendicular to the longitudinal axis of said apparatus.

10. An apparatus, having a longitudinal axis, comprising:
 a. a pair of blunt blades, each of said blades comprising a body portion having a top edge, a contact side, and an opposed external side;
 b. means for longitudinally moving said blades relative to each other between a closed position, in which a portion of the external side of each of said body portions contact each other, and an open position, in which said body portions are spaced apart from each other;

c. means for connecting the body portion of each of said blades to said moving means so that said body portions are rotatable at least partially about an axis substantially perpendicular to the longitudinal axis of said apparatus, wherein each of said body portions rotates between a first position, in which at least a section of said body portion is disposed above or at the same height as the axis about which said body part rotates, and a second position, in which a portion of that section of said body portion disposed above or at the same height as the axis of rotation is disposed below the axis of rotation, wherein each of said connecting means comprises:

i. a support member having a longitudinal edge; and ii. a hinge rotatingly connecting a portion of said support member to a portion of the associated said body portion adjacent the top edge thereof, said hinge having an axis disposed along the axis about which said body portion rotates, wherein said rack has a plurality of teeth longitudinally disposed therein along at least a portion of its length, and wherein said moving means comprises:

i. a longitudinally-extending rack having a length; and ii. means for attaching the respective longitudinal edge of each of said support members to said rack, wherein at least one of said support members is movable along a portion of the length of said rack so that said support members are longitudinally movable relative to each other, wherein said attaching means for each of said support members that is movable comprises an aligning member having an exterior surface and defining a bore therethrough, said bore being of a size to slidably receive said rack therein, a portion of said exterior surface being fixedly attached to the longitudinal edge of said support member and another portion of said exterior surface having a slot therethrough communicating with said bore, said slot being disposed over the teeth in said rack;

d. means for securing said blades at selected longitudinal positions relative to each other, wherein said securing means comprises:

i. a pawl arm having a pawl tooth, said pawl tooth complementarily to the space intermediate two adjacent teeth of said rack;

ii. means for pivotally mounting said pawl arm to a portion of the exterior surface of said aligning member so that said pawl tooth is movable to communicate with the teeth of said rack through the slot of said aligning member; and iii. means for biasing the pawl tooth of said pawl arm toward the teeth of said rack so that said pawl tooth is capable of selectively engaging the teeth of said rack; and e. means for selectively disengaging said securing means, wherein said selective disengaging means comprises a pawl detachment member slidably mounted over at least a portion of the exterior surface of said aligning member, said pawl detachment member being movable between a disengaged position, in which said pawl detachment member is disposed over at least a portion of the slot in said aligning member so that said pawl detachment member is disposed intermediate said pawl tooth and the teeth of said rack to prevent communication therewith, and an engaged position, in which said pawl detachment member is disposed so that said pawl tooth communicates with the teeth of said rack through the slot of said aligning member.

11. An apparatus, having a longitudinal axis, comprising:

a. a pair of blunt blades, each of said blades comprising a body portion having a top edge, a contact side, and an opposed external side;

b. means for longitudinally moving said blades relative to each other between a closed position, in which a portion of the external side of each of said body portions contact each other, and an open position, in which said body portions are spaced apart from each other;

c. means for connecting the body portion of each of said blades to said moving means so that said body portions are rotatable at least partially about an axis substantially perpendicular to the longitudinal axis of said apparatus, wherein each of said body portions rotates between a first position, in which at least a section of said body portion is disposed above or at the same height as the axis about which said body part rotates, and a second position, in which a portion of that section of said body portion disposed above or at the same height as the axis of rotation is disposed below the axis of rotation;

d. means for securing said blades at selected longitudinal positions relative to each other;

e. means for selectively disengaging said securing means; and f. means for detachably engaging said blades with each other when said blades are in the closed position so that both of said blades simultaneously rotate from the first position to the second position as said blades are moved toward each other after engaging with each other.

12. A rib retractor, having a longitudinal axis and being adapted to contact adjacent ribs in a person through an incision, comprising:

a. a longitudinally-extending rack having a length;

b. two support members each having a longitudinal edge;

c. means for attaching the longitudinal edge of each of said support members to said rack wherein at least one of said support members is movable along a portion of the length of said rack so that said support members are longitudinally movable relative to each other;

d. a pair of blunt blades, each of said blades comprising a body portion having a top edge, a contact side, and an opposed external side, said contact side being adapted to contact a selected one of the ribs in the person;

e. a hinge rotatingly connecting a portion of each of said support members to a portion of the body portion of an associated one of said blades adjacent the top edge of said body portion, said hinge having an axis of rotation disposed substantially perpendicular to the longitudinal axis of said rib retractor so that said body portion is rotatable at least partially about an axis, wherein each of said body portions rotates between a first position, in which at least a section of said body portion is oriented substantially parallel to the length of said rack and may be disposed above the incision of the person, and a second position, in which at least a section of said body portion may be disposed into the incision and the contact side of said body portion is oriented to engage the rib;

f. means for securing each of said support members that is movable along said rack at selected positions along the length thereof;

g. means for selectively disengaging said securing means; and h. means for detachably engaging said blades with each other when said blades are in a closed position, in which a portion of the external side of said body portions contact each other, so that both of said blades simultaneously rotate from the first position to the second position as said blades are moved toward each other after engaging with each other.

13. The rib retractor of claim 12, wherein said detachably engaging means comprises a protrusion on the external side of one of said body portions and an indentation on the external side of the other of said body portions, said indentation being of a size to complementarily receive said protrusion therein, wherein when said blades move from the open position to the closed position, said protrusion engages said indentation.

14. An apparatus, having a longitudinal axis, comprising:

a. a first blade;

b. a second blade;

c. a rack having a plurality of teeth therein and a length;

d. an aligning member for movably attaching a portion of said first blade to said rack so that said first blade is movable along a portion of the length of said rack, wherein said aligning member has an exterior surface and defines a bore therethrough, said bore of a size to slidably receive said rack therein, a portion of said exterior surface fixedly attached to a portion of said first blade;

e. means for connecting said second blade to a portion of said rack;

f. a pawl arm having a pawl tooth, said pawl tooth complementarily to a space intermediate two adjacent teeth of said rack;

g. means for mounting said pawl arm to a portion of the exterior surface of said aligning member so that said pawl tooth is movable between being in communication with the teeth of said rack and being spaced apart from said teeth; and h. a barrel member rotatably mounted to said aligning member intermediate said pawl arm and said rack, said barrel member having a latch surface and a delatch surface, said barrel being rotatable between a disengaged position, in which the delatch surface of said barrel contacts a portion of said pawl arm so that said pawl tooth is spaced apart from the teeth of said rack, and an engaged position, in which the latch surface of said barrel contacts said pawl arm so that said pawl tooth communicates with the teeth of said rack.

15. The apparatus of claim 14, wherein said connecting means comprises fixedly attaching a portion of said second blade to a portion of said rod.

16. The apparatus of claim 14, wherein said connecting means comprises a second aligning member movably attaching a portion of said second blade to said rack so that said second blade is movable along a portion of the length of said rack.

17. An apparatus, having a longitudinal axis, comprising:

a. a first blade;

b. a second blade;

c. a rack having a plurality of teeth therein and a length;

d. an aligning member for movably attaching a portion of said first blade to said rack so that said first blade is movable along a portion of the length of said rack, wherein said aligning member has an exterior surface and defines a bore therethrough, said bore of a size to slidably receive said rack therein, a portion of said exterior surface fixedly attached to a portion of said first blade;

e. means for connecting said second blade to a portion of said rack;

f. a pawl arm having a pawl tooth, said pawl tooth complementarily to a space intermediate two adjacent teeth of said rack;

g. means for mounting said pawl arm to a portion of the exterior surface of said aligning member so that said pawl tooth is movable between being in communication with the teeth of said rack and being spaced apart from said teeth; and f. a pawl detachment member slidably mounted over at least a portion of the exterior surface of said aligning member, said pawl detachment member being movable between a disengaged position, in which said pawl detachment member is disposed intermediate said pawl tooth and the teeth of said rack to prevent communication therewith, and an engaged position, in which said pawl detachment member is disposed so that said pawl tooth communicates with the teeth of said rack.

18. An apparatus, having a longitudinal axis, comprising:

a. a pair of blunt blades;

b. a rack having a plurality of teeth therein and a length;

c. means for attaching each of said blades to said rack in which at least one of said blades is movable along said rack so that said blades are longitudinally movable relative to each other between a closed position, in which a portion of each of said blades contact each other, and an open position, in which said blades are spaced apart from each other;

d. a pair of hinges, each hinge rotatably connecting one blade to its respective attaching means so that said blade is rotatable at least partially about an axis substantially perpendicular to the longitudinal axis of said apparatus, wherein each of said blades rotate between a first position and a second position; and e. means for detachably engaging said blades with each other when said blades are in the closed position so that both of said blades simultaneously rotate from the first position to the second position as said blades are moved toward each other after engaging with each other.

* * * * *